United States Patent [19]
Becker et al.

[11] Patent Number: 6,136,008
[45] Date of Patent: Oct. 24, 2000

[54] SKIN ABRADER FOR BIOMEDICAL ELECTRODE

[75] Inventors: Brenda C. Becker; John A. Spevacek, both of Woodbury, Minn.

[73] Assignee: 3M Innovative Properties Company, St. Paul, Minn.

[21] Appl. No.: 09/044,512

[22] Filed: Mar. 19, 1998

[51] Int. Cl.[7] .......................... A61B 17/00; A61B 17/50
[52] U.S. Cl. .................................. 606/131; 600/392
[58] Field of Search ........................... 606/131; 225/77; 600/392, 391

[56] References Cited

U.S. PATENT DOCUMENTS

| | | | |
|---|---|---|---|
| 3,559,856 | 2/1971 | Fehrn-Christensen | 225/77 |
| 3,911,906 | 10/1975 | Reinhold, Jr. | 600/392 |
| 4,459,987 | 7/1984 | Pangburn | 600/131 |
| 4,798,642 | 1/1989 | Craighead et al. | 600/392 |
| 4,954,210 | 9/1990 | Desmond | 156/584 |
| 5,168,875 | 12/1992 | Mitchiner | 600/392 |
| 5,191,887 | 3/1993 | Cartmell | 600/392 |
| 5,228,612 | 7/1993 | Kuo et al. | 225/77 |
| 5,261,402 | 11/1993 | DiSabito | 600/392 |
| 5,330,527 | 7/1994 | Montecalvo | 600/392 |
| 5,658,184 | 8/1997 | Hoopman et al. | 451/28 |
| 5,672,097 | 9/1997 | Hoopman | 451/526 |

FOREIGN PATENT DOCUMENTS

WO 97/24060   7/1997   WIPO ................ A61B 5/0402

*Primary Examiner*—Paul J. Hirsch
*Attorney, Agent, or Firm*—Robert W. Sprague

[57] ABSTRACT

A skin abrader for a biomedical electrode is disclosed wherein the abrader has a geometrically structured surface abrasive selected to provide sufficient abrasive effect to easily remove a portion of the stratum corneum of mammalian skin with minimal skin irritation, in order to reduce skin impedance encountered during diagnosis or monitoring of a mammalian patient.

20 Claims, 1 Drawing Sheet

SKIN ABRADER FOR BIOMEDICAL ELECTRODE

FIELD OF INVENTION

The invention relates to skin abraders for biomedical electrodes. The skin abrader is associated with the electrode to assist removal of a portion of the stratum corneum of a mammalian patient prior to a diagnostic or monitoring procedure that would be affected adversely by skin impedance at the stratum corneum.

BACKGROUND OF INVENTION

Biomedical electrodes are used to either deliver to or receive electrical signals from those mammalian patients. The interface between the mammalian patient and the electrode is the outer layer of mammalian skin, called the stratum corneum. The natural protective nature of the stratum corneum provides an electrical barrier which is typically called skin impedance.

While there are no current maximum amounts of skin impedance recognized by the medical industry in a standard promulgated by the Association for the Advancement of Medicine (AAMI), skin impedance should be minimized to maximize the amount of faint electrical signals emanating from the body when the procedure involves diagnosis or monitoring of an organ of the body producing electrical signals. For example, the amount of skin impedance recognized by some members of the electrode industry for diagnostic medical electrodes ranges from about 1 to about 100 kohm and preferably from about 2 to about 15 kohm, whereas the amount of skin impedance for monitoring medical electrodes ranges from about 1 to about 100 kohm and preferably from about 5 to about 50 kohm. These impedances refer to the impedance of electrode monitoring device and skin together within the first 30 seconds of electrode application on the skin measured at a frequency of 10 Hz using a sinusoidal waveform of low intensity (<10 $\mu$A, peak-peak).

There are three principal means of reducing skin impedance: chemical, electrical and mechanical. A chemical means typically includes providing additional chloride ions ($Cl^-$) between the skin and electrode to increase conductivity through the stratum corneum. An example of an electrical means is disclosed in PCT Patent Publication WO97/24060 (Carim et al.).

The traditional means of reducing skin impedance is mechanically removing a portion of the stratum corneum at the site of biomedical electrode placement on mammalian skin. One commercial skin abrader is a particulate-based strip of material sold by Minnesota Mining and Manufacturing Company of St. Paul, Minn., USA as 3M Skin Prep No. 2236 skin abrader, which instructs a user to tear a piece of material from a roll dispenser and to gently abrade, with moderate pressure, the skin where the electrode will be adhered. The strip is a laminate of mineral particulates on a flexible backing with a coating of adhesive on the opposing side, i.e., adhesive-backed sandpaper having about a 240 grit.

Another type of commercial skin abrader is associated with each individual biomedical electrode sold by Minnesota Mining and Manufacturing Company as 3M Red Dot No. 2249, 2255, 2259, 2260, 2270, 2271, 2274, and 9630 Monitoring Electrodes, where the sandpaper has a grit of about 600 and is a dot of material adhered to the protective release liner of the electrode.

The manufacture of biomedical electrodes is controlled by the various governmental health agencies responsible for assuring that safe and effective products reach the patient. One of the standards required by United States health agencies is called Good Manufacturing Practices (GMP), currently being replaced by Quality Systems Regulations (QSR).

The marketing of biomedical electrodes is subject to price and cost pressures of free enterprise competition among companies and the demands of customers responsible for patients such as health maintenance organizations (HMOs).

While sandpaper made by Minnesota Mining and Manufacturing Company is manufactured according to strict standards, sandpaper has a natural variability from particle to particle. Moreover, a product that relies on sandpaper with mineral composition presents additional manufacturing difficulties in a high-speed, speed, low-cost, GMP/QSR facility.

Minnesota Mining and Manufacturing Company has recently developed a technology that can produce a surface topography that microreplicates each element in the topography. Examples of the microreplication technology is disclosed in U.S. Pat. Nos. 5,672,097 and 5,658,184 and in copending, coassigned, U.S. patent application Ser. No. 08/514,417; now abandoned the disclosures of which are incorporated herein by reference.

SUMMARY OF INVENTION

What is needed in the field of biomedical electrodes is a means of precisely reproducing the topography of a skin abrader that efficiently and effectively removes mechanically a portion of stratum corneum of mammalian skin.

What is also needed is a skin abrader that can be engineered from polymeric material that can be manufactured according to GMP/QSR standards in a cost-effective manner.

The present invention solves both needs by providing a microreplicated skin abrader.

One aspect of the present invention is a skin abrader for a biomedical electrode, comprising polymeric material having a geometrically structured surface abrasive.

A "geometrically structured surface abrasive" for purposes of this application is a precisely engineered topography that can be replicated on a micrometer scale to produce an abrasive surface that can remove portions of the stratum corneum of mammalian skin.

Another aspect of the present invention is a method of making a skin abrader for a biomedical electrode, comprising the steps of (a) forming a film of polymeric material having a geometrically structured surface abrasive, wherein the geometrically structured surface abrasive has a pattern adapted to remove a portion of stratum corneum of mammalian skin; (b) forming a strip from the film, having dimensions selected according to a predetermined means of dispensing the strip; and (c) placing the strip in contact with the dispenser.

A feature of the present invention is a precisely engineered abrader pattern using microreplication technology.

An advantage of the present invention is the ability to make skin abraders for a variety of dispensing means.

Another advantage of the present invention is the ability to cost-effectively make skin abraders under GMP/QSR standards as required for medical devices.

Another advantage is that the present invention requires fewer raw materials leading to a lower probability of adverse skin interaction.

Further features and advantages will be described in conjunction with the following embodiments and drawings.

EMBODIMENTS OF INVENTION

Figure 1:
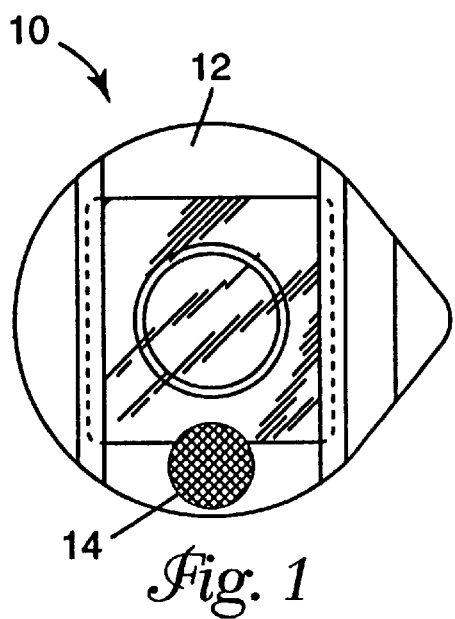
FIG. 1 is a perspective view of one skin abrader of the present invention placed on an individual biomedical electrode.
Figure 2:
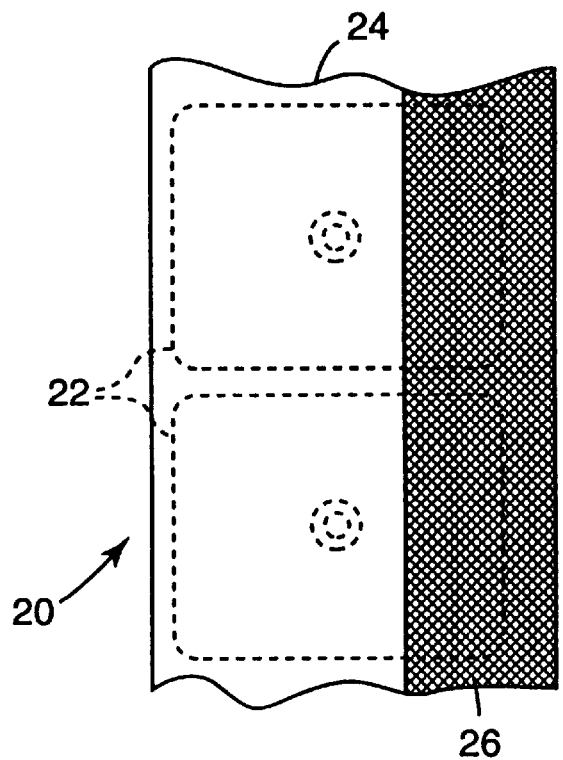
FIG. 2 is a perspective view of another skin abrader of the present invention placed on an array of multiple electrodes.
Figure 3:
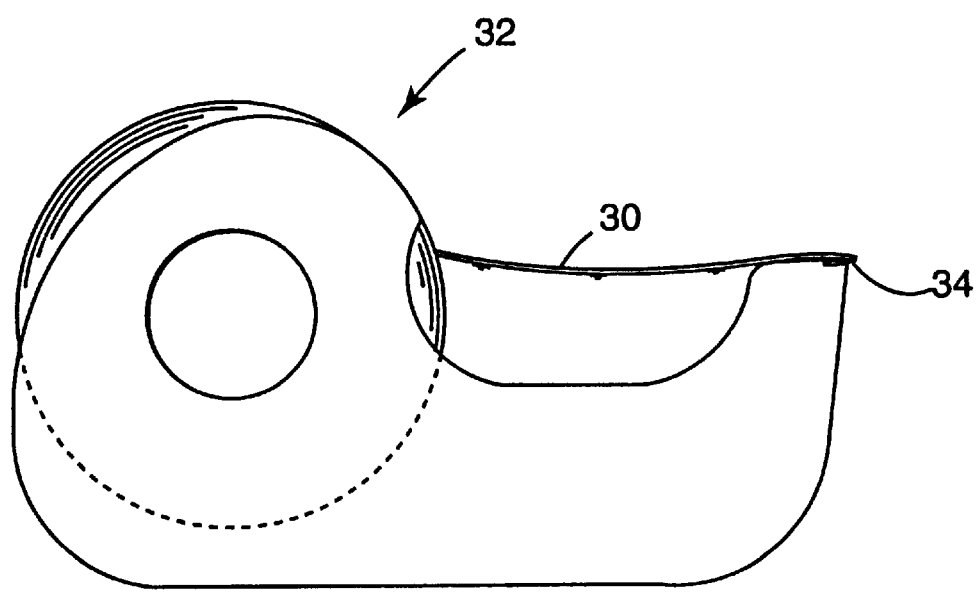
FIG. 3 is a perspective view of a strip of skin abrader of the present invention wound into a tape dispenser.

Skin abraders of the present invention can be used in any of the embodiments seen in FIGS. 1–3.

FIG. 1 illustrates the use of skin abraders of the present invention as a dot on an individual biomedical electrode such as the Red Dot No. 2249, 2255, 2259, 2260, 2270, 2271, 2274, and 9630 Monitoring Electrodes sold by Minnesota Mining and Manufacturing Company (3M) of St. Paul, Minn., USA. Electrode 10 has a protective liner 12 which has an abrader dot 14. In this embodiment, abrader dot 14 has a field of pressure sensitive adhesive on its opposing surface to the geometrically structured surface abrasive to adhere the dot 14 to the protective liner 12.

FIG. 2 illustrates the use of skin abraders of the present invention as a strip on an array of multiple biomedical electrodes on a sheet. Typically the array 20 is a set of individual biomedical electrodes (each 22) adhered to a release liner 24, which on its opposing surface has at least one strip 26 of skin abrader of the present invention. In this embodiment, skin abrader strip 26 has a field of pressure sensitive adhesive on its opposing surface to the geometrically structured surface abrasive to adhere the strip 26 to the release liner 24. Alternatively, one could provide a microreplicated surface which would also serve as the backing itself.

FIG. 3 illustrates the use of skin abraders of the present invention as an abrader strip 30 of microreplicated material to be unwound from a tape dispenser 32 in the same manner as Scotch brand adhesive tape. The dispenser 32 has a serated cutting bar 34 to assist in cutting a piece of the strip 30 from the remainder. In this embodiment, it is optional but preferred to have a field of adhesive on the opposing surface to the microreplicated surface to assist in holding the strip 30 in dispenser 32 and to assist the medical practicioner in using a piece of strip 30 to abrade mammalian skin.

Skin abraders of the present invention are generally constructed according to the teachings of U.S. Pat. Nos. 5,672,097 and 5,658,184 and in copending, coassigned, U.S. patent application Ser. No. 08/514,417; now abandoned which disclosures are incorporated by reference herein. It is within the abilities of one skilled in the art to engineer a microreplicated topographical pattern to tailor the abrasion of stratum corneum of a mammalian patient using the disclosure of, for example, U.S. Pat. No. 5,658,184 and the disclosure of this invention. The principal and unexpected distinction between the uses disclosed in U.S. Pat. No. 5,658,184 and this invention is the necessity to provide a particle-filled geometrically structured surface abrasive for uses with fingernails and toenails in the former, while minimizing such particle-filled geometrically structured surface abrasives for use with various stratum cornea of various mammals. For example, just as the commercial mechanical abraders are offered in various grits, it is possible within the scope of the present invention to provide abraders that have geometrically structured surface abrasives particularly suited for the type of mammal or the type of stratum corneum on an individual species of mammal where the placement of the biomedical electrode is to occur. Preferably, for the stratum corneum for human beings, particles are avoided, although if the electrode were to be attached to the palm of a hand or the heel of a foot, one skilled in the art could adjust the abrasive character of the abraders of the present invention to remove sufficient amount of the stratum corneum in those locations for proper diagnosis or monitoring. Most preferably for all uses involving human beings, because of the GMP/QSR standards and methods of manufacturing, abrasive particles are avoided entirely. This is directly contrary to the teaching of U.S. Pat. No. 5,658,184 which requires abrasive particles for human nail uses. A biomedical electrode is a regulated medical device requiring manufacture according to GMP/QSR standards.

Therefore, parameters of the geometrically structured surface abrasive required for this invention include:

1. a polymeric geometrically structured surface abrasive, which minimizes and preferably avoids any use of mineral particle content, making the assembly of a skin abrader in a high-speed, low-cost biomedical electrode manufacturing facility possible under GMP/QSR conditions; and 2. a predetermined pattern of geometrically structured surface abrasive, which permits assured, engineered surfaces for consistent abrading properties on a specific type of mammalian skin or a specific mammal, in order to achieve reduced skin impedance without undue damage or pain to the patient.

Using these parameters, it is possible to engineer a geometrically structured surface abrasive based upon the tooling used to produce such surface. U.S. Pat. No. 5,658,184 sufficiently describes for purposes of this invention the variety of three-dimensional shapes that are possible in the formation of geometrically structured surface abrasives for use in association with a human body. The three-dimensional shapes can range from regular to random, with a variable pitch as disclosed in U.S. Pat. No. 5,658,184 being preferred.

The vertical dimension (between height and depth) of the geometrically structured surface abrasive can range from about 25 $\mu$m to about 1600 $\mu$m and preferably from about 75 $\mu$m to about 160 $\mu$m. One skilled in the art can choose from various three-dimensional shapes and various vertical dimensions to precisely engineer a geometrically structured surface abrasive suitable for any particular mammalian skin use.

It is possible to engineer a microreplicated surface from a variety of polymeric materials. Nonlimiting examples of such polymers include (meth)acrylates such as triacrylates prepared from one or more monomers such as trimethyolpropane triacrylate and triacrylate of trishydroxyethyl isocyanate. A commercial source for triacrylates is Sartomer Chemical Co. of West Chester, Pa. Other nonlimiting examples are disclosed as binders in U.S. Pat. No. 5,658,184.

Optionally, additives to the microreplicated surface include pigments, dyes, plasticizers, anti-oxidants, and fillers as desired by those skilled in the art.

Skin abrader 10, 20, or 30 can have a total thickness ranging from about 75 to about 2110 $\mu$m and preferably from about 151 to about 414 $\mu$m.

Skin abrader 10, 20, or 30 can have its microreplicated surface formed on any suitable polymeric film. Nonlimiting examples of polymeric material include polyolefins and polyesters, where the polyolefins are typically polyethylenes or polypropylenes. Preferably, the polymeric backing is a polyester material having a thickness ranging from about 50 to about 510 µm and preferably from about 76 to about 254 µm.

Manufacture of skin abrader 10, 20, or 30 can be performed according to the disclosure of U.S. Pat. No. 5,658,184, with adjustments accommodated for the particular microreplicated surface to be engineered. Between the time of formation of the microreplicated surface on the polymeric film and cutting of that film in strips or dots of suitable dimensions, adhesive can be coated on the surface of the film opposing the microreplicated surface. The adhesive can have a coating weight ranging from about 0.419 to about 6.278 mg/cm$^2$ and preferably from about 2.092 to about 4.185 mg/cm$^2$ and can be any suitable pressure sensitive adhesive, preferably those that do not include natural rubber latex for human use. Nonlimiting examples of such adhesives include isoprenes, acrylics, butyl rubber, polyisobutylene, and vinyl ether polymers.

Usefulness of the Invention

Skin abraders of the present invention present a precise and predictable manufacturing component and a precise and predictable stratum corneum impedance reducer for any commercial biomedical electrode that requires abrading of the mammalian skin before use of the electrode.

The entire product line of biomedical electrodes of 3M can benefit from this invention, as well as other biomedical electrodes known to those skilled in the art.

The dimensions and topographies of the geometrically structured surface abrasive skin abraders of the present invention can be varied according to the needs of practitioners in the art of medical diagnosis or monitoring. For example, the dimension and location(s) of the abraders 14 and 26 can be varied according to the requirements of manufacturing and marketing of the biomedical electrodes.

The following examples further disclose embodiments of the invention.

EXAMPLES

For the following examples, two formulations for the formation of the geometrically structured surface abrasive were used. Table 1 shows the formulations.

TABLE 1

| Formulations of Resin | | |
|---|---|---|
| Formulation | Chemical | Wt. Percent |
| A | Trimethyolpropane Triacrylate | 99 |
|   | Benzil Dimethyl Ketal Photoinitiator | 1 |
| B | Trimethyolpropane Triacrylate | 59.5 |
|   | Triacrylate of Trishydroxyethyl Isocyanate | 39.5 |
|   | Benzil Dimethyl Ketal Photoinitiator |   |

Formulations A and B were formed into geometrically structured surface abrasives according to the method disclosed in U.S. Pat. No. 5,658,184 using the pattern disclosed therein, also known as a "VariPitch" pattern, and using a variety of vertical dimensions ranging from about 89 µm (0.0035 inches) to about 254 µm (0.01 inches).

Skin impedance (Z) was measured using an impedance meter with a reference electrode on a human being.

Table 2 shows the results of the various examples with the corresponding skin impedance results. For this experiment, impedances were measured on the arms of 8 people, n=16.

TABLE 2

Panel Results for Various Formulations and Vertical Dimensions of Microreplicated Skin Abrader

| Example | Formulation | Vertical Dimension (µm) | Skin Impedance (Z) (kohm) |
|---|---|---|---|
| 1 | A | 89 | 110 |
| 2 | A | 178 | 58 |
| 3 | A | 254 | 63 |
| 4 | B | 89 | 88 |
| 5 | B | 178 | 39 |
| 6 | B | 254 | 69 |

Table 2 shows the results of the first of two sets of experiments. In this experiment the two formulations described in Table 1 were tested at three different vertical dimensions: 89, 178, and 254 µm. The impedances are given in kohms and were taken 5 seconds after application of the monitoring electrode. These results show that the three most effective of these samples were both 178 µm samples, Formulation A and B, and the 254 µm sample with Formulation B (Examples 2, 3, and 5). These three samples were carried over to be tested again in a separate panel. The results from this second experiment are in Table 3. For this experiment, 13 panelists were tested. Each example of microreplicated abrader was tested twice on the chest of each panelist, n=26.

TABLE 3

Panel Results for Three Examples of Microreplicated Abrader (Repeat Test)

| Example | Formulation | Vertical Dimension (µm) | Skin Impedance (Z) (kΩ) |
|---|---|---|---|
| 7 | A | 178 | 11 |
| 8 | A | 254 | 5 |
| 9 | B | 178 | 15 |

Example 8 gave the lowest impedance in this panel; however it was observed that the skin irritated due to the higher level of skin abrasion. From this experiment, it was determined that Example 7, the microreplicated skin abrader with vertical dimension of 178 µm and Formulation A provided the most effective abrasion without skin irritation. Depending on the geometrical shape and size of the abrading pattern, the relationship of vertical dimension versus skin impedance may change. This may be particularly true if the variable is the electrode electrolyte such as wet gel, solid gel, or conductive adhesive with differing firmness.

The invention is not limited to the above embodiments. The claims follow.

What is claimed is:

1. A skin abrader for a biomedical electrode, comprising: polymeric material having a geometrically structured surface abrasive, wherein the polymeric material is free of abrasive particles.

2. The abrader of claim 1, wherein the geometrically structured surface abrasive has a pattern with a pitch between a height and a depth in the topography ranging from regular to random.

3. The abrader of claim 2, wherein the pitch is variable and wherein the vertical dimension between the height and the depth ranges from about 25 µm and 1524 µm.

4. The abrader of claim 1, wherein the polymeric material further comprises an opposing surface opposite the geometrically structured surface abrasive, and further wherein the opposing surface of the polymeric material is adhered to a protective liner of a biomedical electrode.

5. The abrader of claim 1, wherein the polymeric material is a strip having dimensions adapted to be dispensed from a dispenser.

6. The abrader of claim 1, wherein the polymeric material is a strip having dimensions adapted to be adhered to a sheet associated with at least one biomedical electrode.

7. The abrader of claim 1, wherein the polymeric material comprises polymers prepared from monomers of triacrylates.

8. The abrader of claim 1, wherein the polymeric material further comprises pigments, dyes, plasticizers, anti-oxidants, or fillers.

9. The abrader of claim 3, wherein the pitch is variable and wherein the vertical dimension between the height and the depth ranges from about 85 $\mu$m and 254 $\mu$m.

10. A method of making a skin abrader for a biomedical electrode, comprising:
  (a) forming a film of polymeric material having a geometrically structured surface abrasive, wherein the geometrically structured surface abrasive has a pattern adapted to remove a portion of stratum corneum of mammalian skin and further wherein the polymeric material is free of abrasive particles;
  (b) separating a portion of the film to form an abrader strip; and
  (c) placing the abrader strip in contact with a dispenser.

11. The method of claim 10, further comprising coating an adhesive on the film before separating the film to form the abrader strip.

12. The abrader of claim 1, wherein the polymeric material further comprises an opposing surface opposite the geometrically structured surface abrasive, and further wherein the opposing surface of the polymeric material is adhered to a biomedical electrode.

13. A skin abrader for a biomedical electrode, comprising polymeric material having a geometrically structured surface abrasive, wherein the polymeric material is free of abrasive particles, and further wherein the geometrically structured surface abrasive has a pattern with a pitch between a height and a depth in the topography that is variable, and still further wherein the vertical dimension between the height and the depth ranges from about 25 $\mu$m and 1524 $\mu$m.

14. The abrader of claim 13, wherein the polymeric material comprises polymers prepared from monomers of triacrylates.

15. An article comprising:
  a biomedical electrode; and
  a skin abrader comprising polymeric material having a geometrically structured surface abrasive, wherein the polymeric material is free of abrasive particles.

16. The article of claim 15, wherein the skin abrader is adhered to the biomedical electrode.

17. The article of claim 15, wherein the biomedical electrode comprises a protective liner, and further wherein the skin abrader is adhered to the protective liner.

18. The article of claim 15, wherein the polymeric material comprises polymers prepared from monomers of triacrylates.

19. The article of claim 15, wherein the geometrically structured surface abrasive has a pattern with a pitch between a height and a depth in the topography ranging from regular to random.

20. The article of claim 19, wherein the pitch is variable and wherein the vertical dimension between the height and the depth ranges from about 25 $\mu$m and 1524 $\mu$m.

* * * * *